US006186977B1

(12) United States Patent
Andrews et al.

(10) Patent No.: US 6,186,977 B1
(45) Date of Patent: *Feb. 13, 2001

(54) APPARATUS AND METHOD FOR TOTAL INTRAVENOUS ANESTHESIA DELIVERY AND ASSOCIATED PATIENT MONITORING

(75) Inventors: Thomas W. Andrews; Louis M. Guzzi; David P. Hartson, all of Longwood; James L. Riley, Winter Park, all of FL (US)

(73) Assignee: Joseph L. Riley Anesthesia Associates, Maitland, FL (US)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

This patent is subject to a terminal disclaimer.

(21) Appl. No.: 08/847,557

(22) Filed: Apr. 24, 1997

(51) Int. Cl.[7] .................................................. A61M 31/00
(52) U.S. Cl. .................................................. 604/67; 604/30
(58) Field of Search ................................... 604/30, 31, 49, 604/50, 65–67, 246, 131; 128/DIG. 12, DIG. 13

(56) References Cited

U.S. PATENT DOCUMENTS

| | | | |
|---|---|---|---|
| 4,237,925 | 12/1980 | Urushida | 137/552 |
| 4,308,866 | 1/1982 | Jelliffe et al. | 128/214 |
| 4,681,378 | 7/1987 | Hellman, III | 312/108 |
| 4,756,706 | 7/1988 | Kerns et al. | 604/66 |
| 5,419,316 | 5/1995 | Bernstein | 128/203.12 |
| 5,466,700 | * 11/1995 | Batenhorst et al. | 514/329 |
| 5,560,352 | 10/1996 | Heim et al. | 128/203.12 |
| 5,895,371 | * 4/1999 | Levitas et al. | 604/49 |

FOREIGN PATENT DOCUMENTS 0 401 579    12/1990    (EP) ............................ A61B/219/02

OTHER PUBLICATIONS

Courtiss et al., *Plastic & Reconstructive Surgery*, "Anesthetic Practices in Ambulatory Aesthetic Surgery", (Apr. 1945) pp. 792–795.
Wender, "Office–Based Anesthesia How I Do It" (7 pages).
Joas, *American Society of Anesthesiologist Newsletters*, "Practice Options: Office–Based Anesthesia: An Overview" (1997) pp. 1–3.
Weiser, *SOBA Clinical Forum*, "Monitoring" (Mar. 9, 1998).

(List continued on next page.)

*Primary Examiner*—Manual Mendez
(74) *Attorney, Agent, or Firm*—Allen, Dyer, Doppelt, Milbrath & Gilchrist, P.A.

(57) ABSTRACT

An apparatus for total intravenous anesthesia includes at least one supply and infusion pump for an intravenous anesthesia agent carried by the apparatus housing, and at least one monitor for monitoring the characteristics of the patient during the total intravenous anesthesia. The at least one intravenous anesthesia agent preferably includes a first intravenous anesthesia agent, and more preferably, an analgesic, having a relatively quick offset so that the effects wears off relatively quickly upon stopping intravenous infusion. For monitoring the patient, the apparatus preferably includes at least one of an electrocardiogram, a blood oxygen monitor, a blood carbon dioxide monitor, inspiration/expiration oxygen, inspiration/expiration carbon dioxide, a blood pressure monitor, a pulse rate monitor, a respiration rate monitor, and a patient temperature monitor, for example. The first intravenous anesthesia agent may be an esterase metabolized opioid, such as remifentanil. A second supply of a second intravenous anesthesia agent carried by the housing may also be included. The second supply may be another anesthesia agent, such as propofol, for example. Method aspects of the invention are also disclosed.

45 Claims, 2 Drawing Sheets

OTHER PUBLICATIONS

Wiener, *SOBA Clinical Forum,* "Monitoring" (Jan. 13, 1998).

Perkins, *SOBA Clinical Forum,* "Monitoring" (Jan. 12, 1998).

Armistead, *SOBA Clinical Forum,* "Costs of Office Based Anesthesia" (Jun. 18, 1998).

Hogue, Jr. et al., "A Multicenter Evaluation of Total Intravenous Anesthesia with Remifentanial and Propofol for Elective Inpatient Surgery", *Anesth Analog* 1994, pp. 279–285.

Dershwitz et al., "Initial Clinical Experience with Remifentanil, a New Opioid Metabolized by Esterases", *Anesth Analog* 1995, pp. 619–623.

Advertisement regarding the Banyan Stat Kit®.

Carl C. Hug, Jr., M.D., Ph.D., *APSFS Newletter,* "Remifentanil—Safety Issues With a New Opioid Drug" (1996).

*CenterWatch Newly Approved Drug Therapies Listing,* Ultiva (remifentanil hydrochloride) (1996).

Gavin Kenny et al., *Infusion Anaesthesia,* Propofol Infusion Anaesthesia.

Bill Dial, *Anesthesiology News,* "Office–Based Anesthesia: A New Subspecialty Developed in Modern Economic Environment", (Mar. 1997).

S. Olofsen, *The Dutch Anesthesiology Corner,* "Introduction to T.C.I." (1996).

Ohmeda Product Information, *Anesthesia Delivery Systems,* "Excel SE Series Anesthesia Systems" (1996).

*Medical Sciences Bulletin,* "Opiod Analgesic Remifentanil Approved" (1996).

\* cited by examiner

APPARATUS AND METHOD FOR TOTAL INTRAVENOUS ANESTHESIA DELIVERY AND ASSOCIATED PATIENT MONITORING

FIELD OF THE INVENTION

The present invention relates to the field of medical devices and procedures, and, more particularly, to an apparatus and related methods for administering anesthesia.

BACKGROUND OF THE INVENTION

There is a continuing trend in health care to significantly reduce and replace in-patient hospital care with ambulatory care. For example, ambulatory surgery now accounts for over 60% of all operations performed in the United States, and is expected to increase to 80% of all procedures by the year 2000. This trend is likely to continue as surgeons embrace the ongoing development of minimally invasive surgical techniques, as third party payers reduce or restrict payments for health care, and as the acceptance by patients and society grows for ambulatory care.

The traditional delivery of anesthesia for in-patient hospital care typically relies heavily on the use of inhalation anesthesia agents. For example, the Excel series anesthesia systems from Ohmeda include a hypoxic guard, sophisticated electronic ventilation, flow management systems, vaporization and breathing circuits. The systems offer a choice of monitors, vaporizers, ventilators, and offer drawers or shelves for storage. Unfortunately, the bulkiness of even advanced conventional inhalation equipment severely hinders the portability of the equipment and thereby limits the possible locations where the equipment may be used.

Another significant shortcoming for traditional inhalation anesthesia systems is that scavenging or ventilation systems are required by various governmental regulations, such as OSHA regulations in the United States. In other terms, complicated and expensive room ventilation as in a traditional operating theater is needed for conventional inhalation systems to comply with various regulations.

As reported in the March 1997 issue of Anesthesiology News, "[t]he transition from the hospital to the free-standing surgical center to the office surgical suite continues to escalate." Accordingly, the ambulatory trend in health care creates new geographic sites that may be desirably served by an unburdened anesthesia delivery system.

There are several anesthesia techniques which do not necessarily require the use of vaporized inhalants. Total intravenous infusion anesthesia (TIVA) uses liquid intravenous agents in place of the conventional vaporized inhalants. Along these lines, target controlled infusion (TCI) is a way of administering an intravenous anesthesia agent using a computer to monitor the patient and control an infusion pump. Using a computer with a pharmacokinetic program permits control of a desired plasma concentration of an agent, such as propofol, without overshooting the desired level.

Unfortunately, conventional intravenous agents for TIVA or TCI may have relatively long offset times, that is, relatively long times before the anesthesia and other effects wear off in the patient. Some agents may result in active metabolites that additionally remain for a relatively long time after stopping delivery of the anesthesia. Moreover, a quick onset and quick offset analgesia agent has not been previously available. In view of the prior shortcomings of conventional TIVA agents, there has been no incentive to develop efficient integrated platforms for using TIVA or TCI in an ambulatory setting.

SUMMARY OF THE INVENTION

In view of the foregoing background, it is therefore an object of the present invention to provide an apparatus and associated methods for delivering total intravenous anesthesia to a patient, such as in an ambulatory setting.

It is another object of the present invention to provide a compact and efficient integrated apparatus and associated methods for delivering total intravenous anesthesia to a patient and while providing monitoring of important patient characteristics.

These and other objects, advantages, and features of the present invention are provided by an apparatus for total intravenous anesthesia which comprises at least one supply and delivery means for an intravenous anesthesia agent carried by the apparatus housing, and at least one monitor for monitoring a characteristic of the patient. Moreover, the at least one intravenous anesthesia agent preferably includes a first intravenous anesthesia agent having a relatively quick offset so that the effects thereof wear off relatively quickly upon stopping the intravenous infusion. Intravenous infusion of the at least one anesthetic agent results in total intravenous anesthesia in the patient and without using an inhaled anesthesia agent.

For monitoring the patient, the apparatus preferably includes one or more monitors carried by the apparatus housing for monitoring patient characteristics. The monitors may include one or more of an electrocardiogram, a blood oxygen monitor, a blood carbon dioxide monitor, an inspiration oxygen monitor, an expiration oxygen monitor, an inspiration carbon dioxide monitor, an expiration carbon dioxide monitor, a blood pressure monitor, a pulse rate monitor, a respiration rate monitor, and a patient temperature monitor, for example. Any of these monitors, or combinations of monitors may be included in the relatively compact housing of the apparatus. In addition, the apparatus may also include at least one recorder cooperating with the monitors to provide a record of a respective monitored patient characteristics.

Also relating in part to monitoring, the apparatus may also preferably include telecommunication means carried by the housing to be available for providing a telemetry and/or voice communications channel to another site. The telecommunications means may include a wireless transceiver, such as a transceiver for cellular telephone communications.

The apparatus also preferably includes a back-up battery power supply carried by the housing so that the apparatus is operable in the event of a power outage. The housing also desirably has an upper surface defining a horizontal work surface. In addition, wheels or castors may be provided on the housing of the apparatus to increase its portability. A storage cabinet may also be associated with the housing of the apparatus for storing consumables used for total intravenous anesthesia.

Returning again to the first anesthesia agent, the first relatively quick offset anesthesia agent is preferably a quick onset and quick offset analgesia agent. The relatively quick offset is preferably defined by a relatively short biological half-life not greater than about 10 minutes. For example, the first intravenous anesthesia agent may comprises an esterase metabolized opioid, such as remifentanil. A second supply of a second intravenous anesthesia agent carried by the housing may also be included. The second supply may be another anesthesia agent, such as the amnestic propofol, for example.

A method aspect of the invention is for administering total intravenous anesthesia to a patient. The method preferably comprises the step of providing a housing carrying at least one supply of an intravenous anesthesia agent, at least one infusion pump for delivering the intravenous anesthesia agent, and at least one patient characteristic monitor. The method also preferably includes the step of controllably intravenously delivering the intravenous anesthesia agent to the patient from the supply carried by the housing and using the infusion pump also carried by the housing so that total intravenous anesthesia is achieved in the patient.

Moreover, the at least one intravenous anesthesia agent is preferably provided by a first intravenous analgesic having a relatively quick offset so that effects wear off relatively quickly upon stopping intravenous infusion. The method also preferably includes the step of monitoring at least one patient characteristic using the associated patient characteristic monitor carried by the housing during administration of total intravenous anesthesia. For example, the step of monitoring may include monitoring one or more of the patient's heart activity, blood oxygen level, carbon dioxide blood level, blood pressure, pulse rate, respiration rate and temperature.

The method may also include the step of providing the housing including a telecommunications transceiver. Accordingly, the method may further include the step of using the telecommunications transceiver for providing at least one of telemetry and voice communications during administration of total intravenous anesthesia.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
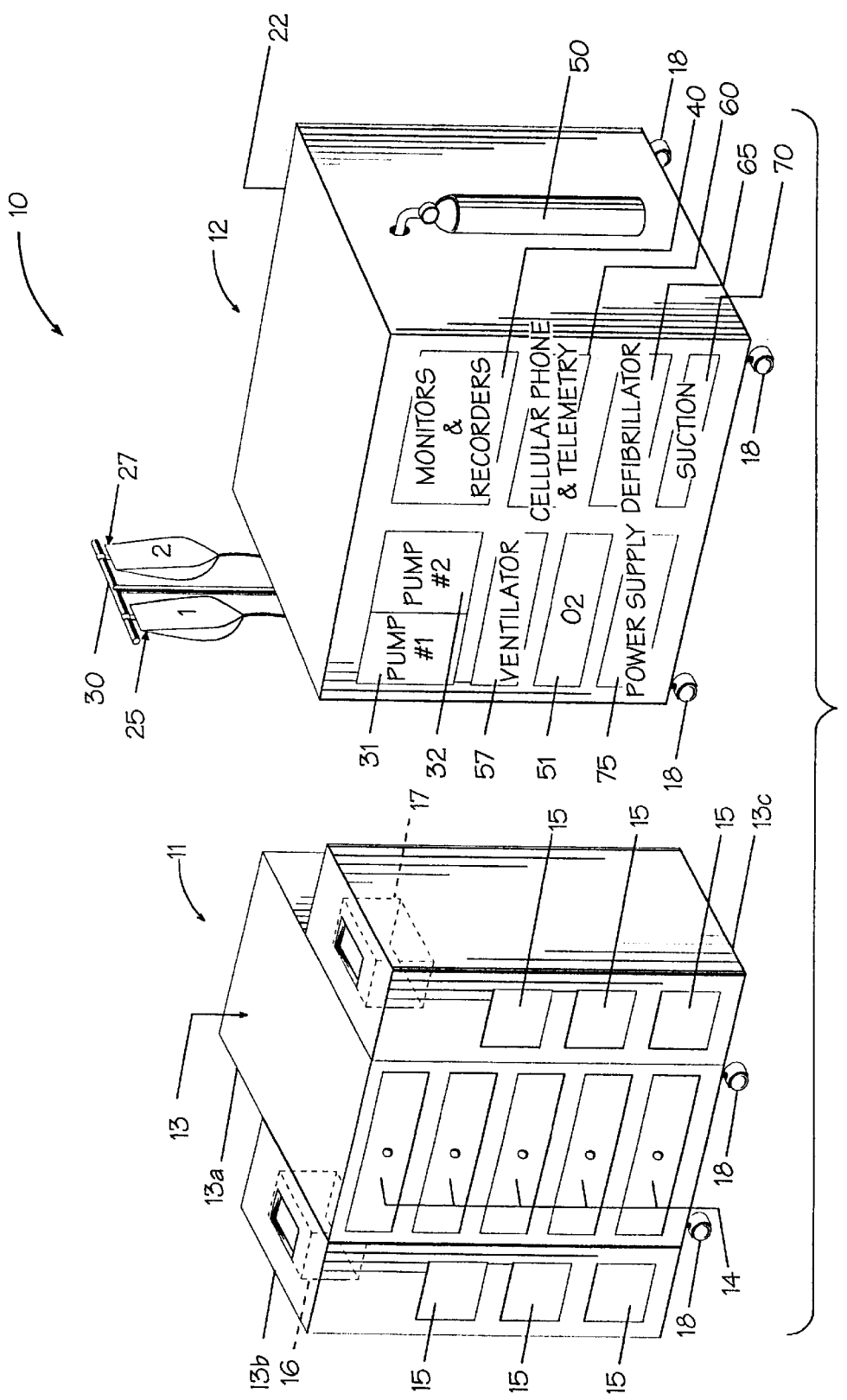
FIG. 1 is a perspective view of an embodiment of the apparatus according to the invention with certain portions illustrated schematically.

The apparatus in accordance with the invention is generally designated by reference numeral 10 in the drawings. In one embodiment of the apparatus 10 as shown in FIG. 1, the apparatus includes a first or storage platform 11 for the storage of consumable materials, and for the temporary collection of waste materials. The apparatus 10 also illustratively includes a second or anesthesia platform 12 more particularly for the administration of total intravenous anesthesia in accordance with the invention.

The storage platform 11 is essentially a portable cabinet and illustratively includes a housing 13 having a first or central portion 13a and side wing portions 13b, 13c which may be swung to the open position, as illustrated, or moved to a closed position covering the front of the central portion as would be readily understood by those skilled in the art. Generic storage bins or areas 15 are illustrated in the side portions 13b, 13c. The central portion 13a is also equipped in the illustrated embodiment with a plurality of sliding drawers 14. Yet another feature of the storage platform 11 is the provision of one or more temporary waste collection bins. In the illustrated embodiment, a first waste bin 16 is for typical waste, such as used rubber gloves, etc. A second waste bin 17 may be used for sharps, for example, and as would be readily understood by those skilled in the art.

The housing 13 of the storage platform 11 is preferably relatively compact, yet efficient in its use of space. It may also be preferred to include wheels or castors 18 on the bottom of the housing 13 to permit the platform 11 to be readily moved. The storage platform 11 may also include one or more locks for security. The housing 13 of the storage platform 11 may also define a generally horizontal upper surface which may be used as a work surface during anesthesia administration.

Those of skill in the art will readily appreciate other configurations for the storage platform 11. For example, in other embodiments the storage platform 11 may be connected to the anesthesia platform 12. The separate platforms 11, 12 as illustrated may be desirable for transporting the apparatus 10, or for facilitating restocking of supplies and removal of waste from the first platform 11. The shelving, storage bins, and waste bins can have other configurations as would also be appreciated by those skilled in the art.

Figure 2:
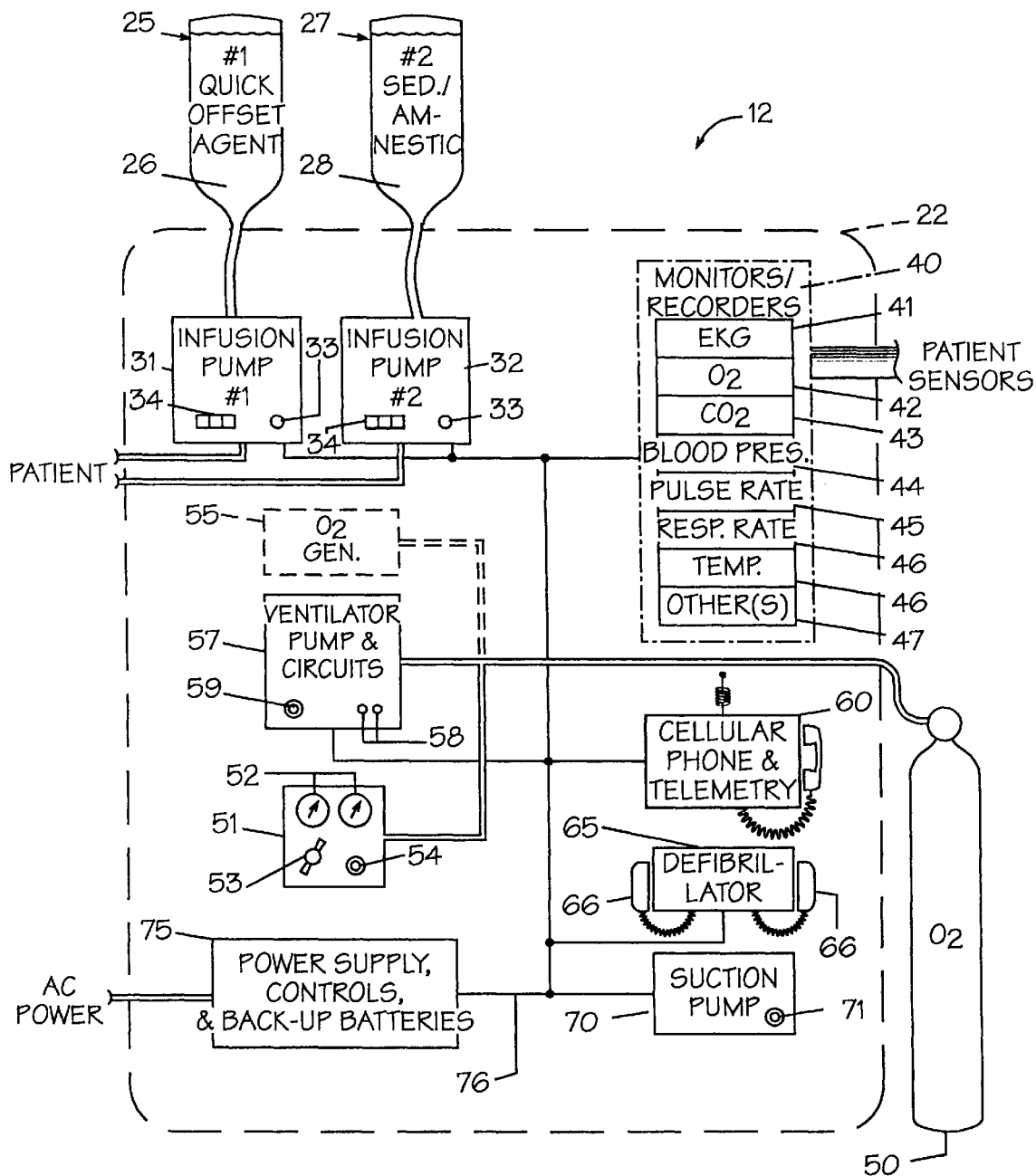
FIG. 2 is a schematic block diagram illustrating portions of the apparatus as shown in FIG. 1 in greater detail.

Turning now to the right hand portion of FIG. 1, and the more detailed schematic diagram of FIG. 2, the second or anesthesia platform 12 is now described in greater detail. The anesthesia platform 12 includes a generally rectangular housing 22, which is also illustratively mounted on wheels or castors 18 for portability. The upper portion of the housing 22 also defines an usable work surface. An intravenous (IV) bag support 30 illustratively carries two IV supplies in the form of bags 25, 27. The IV bag support 30 may be telescoping, collapsible or otherwise removable to further facilitate portability of the anesthesia platform 12.

The first IV bag 25 carries a first anesthesia agent 26, and the second bag 27 carries the corresponding second agent 28. In addition, the flow of the first and second intravenous anesthesia agents 26, 28 is controlled in the illustrated embodiment by corresponding first and second infusion pumps 31, 32. The pumps include controls 33, such as for setting flow rates, as well as indicators 34 of the volume delivered, which are schematically illustrated in FIG. 2. Other intravenous delivery means are also contemplated by the present invention, as would be readily understood by those skilled in the art. For example, infusion pumps 31, 33 may not be needed in other embodiments of the invention.

One aspect of the present invention is based upon the recent development of a quick acting and quick offset analgesic agent, remifentanil, by Glaxo Wellcome. More particularly, remifentanil is an ultra short acting analgesic with a relatively short biological half-life of about 6 to 10 minutes. Remifentanil is an esterase metabolized opioid which leaves no active metabolites. The extremely rapid achievement of the peak effect for any dose makes it relatively easy to recognize the dose-effect relationship and facilitates titration of dose versus effect, allowing rapid control of responses to noxious or painful stimuli. Accordingly, in one embodiment of the invention the first anesthesia agent 26 delivered by the anesthesia platform 12 is remifentanil hydrochloride. Other similar quick offset agents may also be developed and used as would be readily understood by those skilled in the art.

For total intravenous anesthesia using remifentanil as the first agent 26, it may also be preferred to include a second anesthesia agent 28. In particular, Zeneca's propofol may be used as the second agent 28, and which is generally considered to be an ultra short acting amnestic. Propofol may sometimes be considered as at least partially a hypnotic or sedative agent as would be readily understood by those skilled in the art. Propofol, like remifentanil, also leaves virtually no active metabolites. Another suitable amnestic anesthesia agent may be midazolam, for example, as would also be readily understood by those skilled in the art.

In other embodiments, the second intravenous anesthesia agent 28 may be at least one of an amnesia, analgesia, muscle relaxation and sedation agent. The second intravenous anesthesia agent 28 may preferably induce and maintain general anesthesia as does propofol, for example. In yet another embodiment, the second intravenous anesthesia agent may be the same as the first intravenous anesthesia agent to thereby provide a back-up to the first supply 25 and the first infusion pump 31. Of course, other intravenous anesthesia agents may also be used in conjunction with the first and second agents described above, and as would be readily understood by those skilled in the art.

It is recognized by the invention that the combination of the currently available agents, remifentanil and propofol, or like agents with rapid half-lives and virtually no active metabolites, facilitate total intravenous anesthesia in the out-patient setting. Cost effectiveness may also be realized by decreasing recovery room times which may be further realized and potentially beneficial in outcome based medicine.

To effectively deliver the anesthesia as described above and also meet typical regulatory and medical guidelines, adequate patient monitoring is also desired. Accordingly, the anesthesia platform 12 also includes monitors for monitoring patient characteristics. In addition, since it may also be desirable to record the monitored characteristics, the illustrated embodiment includes schematically illustrated monitors/recorders 40 for patient characteristics. More particularly, as shown in FIG. 2, the monitors/recorders 40 may include: an electrocardiogram (EKG) 41; an oxygen monitor 42 for one or more of blood oxygen level, an inspired oxygen level, and an expired oxygen level; a carbon dioxide monitor 43 for one or more of blood carbon dioxide level, an inspired carbon dioxide level, and a expired carbon dioxide level; a blood pressure monitor 44, a pulse rate monitor 45, a respiration rate monitor 46, a patient temperature monitor 46, and one or more other monitors 47 as would be readily understood by those skilled in the art.

As would also be understood by those skilled in the art, the various monitors/recorders 40 may be any of several types commercially offered by a number of medical device manufacturers and distributors. Of note, the monitors/recorders 40 are desirably relatively compact to permit the overall anesthesia platform 12 to also be relatively compact. The monitors/recorders 40 may also desirably be modular to facilitate replacement and repair. Multiple component monitors from various manufacturers can be modified, packaged, and compartmentalized into the single, stand-alone anesthesia platform 12 as illustrated.

Also somewhat relating to monitoring of the patient, the anesthesia platform 12 may also include telecommunications means for providing one or both of a telemetry channel or a voice communications channel to a remote location. In the illustrated embodiment, a cellular telephone 60 may provide one or both of telemetry and telephone functions via the cellular telephone network as would be readily understood by those skilled in the art. The cellular telephone 60 may be beneficial in that it allows the anesthesia platform 12 to be positioned and relocated without concern for hardwired connections to the telephone network, yet the telephone or telemetry capability is readily available along with the other devices carried by the platform.

The illustrated anesthesia platform 12 also includes other devices and/or systems conveniently packaged within or carried by the overall housing 22. Moreover, these devices may provide highly desirable care during total intravenous anesthesia. In other words, these devices may provide basics for care and, in particular, may provide the basics for short term resuscitation of the patient. For example, the anesthesia platform 12 carries an oxygen cylinder 50, as oxygen may typically be used during the anesthesia. The oxygen may be made available for delivery to the patient via a control panel 51 including one or more gages 52, control valves 53, and outlet ports 54, as schematically illustrated in FIG. 2. Alternately or in addition to the oxygen cylinder 50, oxygen may be generated and supplied via the control panel 51 by a conventional oxygen generator 55 as would be readily understood by those skilled in the art.

The anesthesia platform 12 may also preferably carry a ventilator pump and circuits 57 operable via the schematically illustrated controls 58 and deliver ventilation through the schematically illustrated outlet port 59. Of course, the ventilator is also illustratively connected to the oxygen supply as would be readily understood by those skilled in the art.

For other procedures as would be appreciated by those skilled in the art, the platform 12 also carries a defibrillator 65 and a suction pump 70. The defibrillator 65 also includes paddles or electrodes 66 to be applied to the patient as would also be readily understood by those skilled in the art. The suction pump 70 makes suction available via the illustrated port 71.

Yet another aspect of the anesthesia platform 12 is that it can be self-powered, such as during a utility system power outage. Accordingly, the platform 12 includes the schematically illustrated power supply 75 which may include controls, auxiliary power outlets, and also rechargeable back-up batteries as would be readily understood by those skilled in the art. The various other electrically powered devices may be fed power from the power supply 75 via the illustrated power bus 76.

Those of skill in the art will recognize that the anesthesia platform 12 may include yet other monitoring and devices for performing short term resuscitation or other procedures. In addition, one or more storage compartments may be provided in the housing 22. The anesthesia platform 12 contains those items for delivering total intravenous anesthesia, including support drugs, and equipment organized in a methodical, ergonomical and reproducible fashion. Field support for the storage platform 11 and anesthesia platform 12 of the illustrated apparatus 10 may be through the creation of an organization and system to provide maintenance, resupply, resterilization, service, and associated documents as would be readily understood by those skilled in the art.

The present invention may be used in many applications, particularly for ambulatory surgery, such as, for example, for cosmetic surgery, dermatology, dentistry and podiatry. Associated applications may likely include critical care services in transport, military applications, MRI, and commercial airlines. Accordingly, many modifications and other embodiments of the invention will come to the mind of one skilled in the art having the benefit of the teachings presented in the foregoing descriptions and the associated That which is claimed is:

1. An apparatus for administering total intravenous anesthesia to a patient, the apparatus comprising:
   a housing;
   at least one supply of at least one intravenous anesthesia agent carried by the housing;
   intravenous delivery means carried by the housing for controllably intravenously delivering said at least one intravenous anesthesia agent to the patient so that total intravenous anesthesia is achieved in the patient and without an inhaled anesthesia agent;
   said at least one intravenous anesthesia agent comprising a first intravenous anesthesia agent having a relatively quick offset so that effects thereof wear off relatively quickly upon stopping intravenous infusion; and
   at least one monitor carried by said housing for monitoring at least one patient characteristic during total intravenous anesthesia of the patient, the at least one monitor comprising an electrocardiogram.

2. An apparatus according to claim 1 wherein said at least one monitor also comprises a blood oxygen monitor.

3. An apparatus according to claim 1 wherein said at least one monitor also comprises a blood carbon dioxide monitor.

4. An apparatus according to claim 1 wherein said at least one monitor also comprises one of an inspiration and expiration oxygen monitor.

5. An apparatus according to claim 1 wherein said at least one monitor also comprises one of an inspiration and expiration carbon dioxide monitor.

6. An apparatus according to claim 1 wherein said at least one monitor also comprises a blood pressure monitor.

7. An apparatus according to claim 1 wherein said at least one monitor also comprises a pulse rate monitor.

8. An apparatus according to claim 1 wherein said at least one monitor also comprises a respiration rate monitor.

9. An apparatus according to claim 1 wherein said at least one monitor also comprises a patient temperature monitor.

10. An apparatus according to claim 1 further comprising at least one recorder cooperating with said at least one monitor to provide a record of a respective monitored patient characteristic.

11. An apparatus according to claim 1 wherein aid at least one supply comprises at least one intravenous fluid bag; and wherein said intravenous infusion means comprises at least one intravenous infusion pump.

12. An apparatus according to claim 1 wherein said first intravenous anesthesia agent comprises an analgesic.

13. An apparatus according to claim 1 wherein the relatively quick offset of said first intravenous anesthesia agent is defined by a relatively short biological half-life not greater than about 10 minutes.

14. An apparatus according to claim 1 wherein said first intravenous anesthesia agent comprises an esterase metabolized opioid.

15. An apparatus according to claim 1 wherein said first intravenous anesthesia agent comprises remifentanil.

16. An apparatus according to claim 1 further comprising telemetry means carried by said housing and cooperating with said at least one monitor for providing telemetry for the at least one patient characteristic.

17. An apparatus for administering total intravenous-anesthesia to a patient, the apparatus comprising:
   a housing;
   at least one supply of at least one intravenous anesthesia agent carried by the housing;
   intravenous delivery means carried by the housing for controllably intravenously delivering said at least one intravenous anesthesia agent to the patient so that total intravenous anesthesia is achieved in the patient and without an inhaled anesthesia agent;
   said at least one intravenous anesthesia agent comprising a first intravenous anesthesia agent having a relatively quick offset so that effects thereof wear off relatively quickly upon stopping intravenous infusion;
   at least one monitor carried by said housing for monitoring at least one patient characteristic during total intravenous anesthesia of the patient; and
   telemetry means carried by said housing and cooperating with said at least one monitor for providing telemetry for the at least one patient characteristic, wherein said telemetry means comprises a wireless transceiver operable over a cellular telephone network.

18. An apparatus for administering total intravenous anesthesia to a patient, the apparatus comprising:
   a housing;
   at least one supply of at least one intravenous anesthesia agent carried by the housing;
   intravenous delivery means carried by the housing for controllably intravenously delivering said at least one intravenous anesthesia agent to the patient so that total intravenous anesthesia is achieved in the patient and without an inhaled anesthesia agent;
   said at least one intravenous anesthesia agent comprising a first intravenous anesthesia agent having a relatively quick offset so that effects thereof wear off relatively quickly upon stopping intravenous infusion;
   at least one monitor carried by said housing for monitoring at least one patient characteristic during total intravenous anesthesia of the patient; and
   voice channel means carried by said housing for providing a voice communications channel.

19. An apparatus according to claim 18 wherein said voice channel means comprises a wireless transceiver operable over a cellular telephone network.

20. An apparatus according to claim 1 further comprising a battery carried by said housing for powering the apparatus.

21. An apparatus according to claim 1 wherein said housing has an upper surface defining a horizontal work surface.

22. An apparatus according to claim 1 further comprising castor means on a lower portion of said housing to permit relocation of said housing.

23. An apparatus according to claim 1 wherein said at least one supply comprises a second supply of a second intravenous anesthesia agent carried said housing.

24. An apparatus for administering total intravenous anesthesia to a patient, the apparatus comprising:
   a housing;
   at least one supply of at least one intravenous anesthesia agent carried by the housing;
   intravenous delivery means carried by the housing for controllably intravenously delivering said at least one intravenous anesthesia agent to the patient so that total intravenous anesthesia is achieved in the patient and without an inhaled anesthesia agent;
   said at least one intravenous anesthesia agent comprising a first intravenous anesthesia agent having a relatively quick offset so that effects thereof wear off relatively quickly upon stopping intravenous infusion; and at least one monitor carried by said housing for monitoring at least one patient characteristic during total intravenous anesthesia of the patient;

wherein said at least one supply comprises a second supply of a second intravenous anesthesia agent carried by said housing, and wherein said first intravenous anesthesia agent comprises an analgesic, and wherein said second intravenous anesthesia agent comprises a relatively quick offset amnestic.

25. An apparatus for administering total intravenous anesthesia to a patient, the apparatus comprising:

a housing;

at least one supply of at least one intravenous anesthesia agent carried by the housing;

intravenous delivery means carried by the housing for controllably intravenously delivering said at least one intravenous anesthesia agent to the patient so that total intravenous anesthesia is achieved in the patient and without an inhaled anesthesia agent;

said at least one intravenous anesthesia agent comprising a first intravenous anesthesia agent having a relatively quick offset so that effects thereof wear off relatively quickly upon stopping intravenous infusion;

at least one monitor carried by said housing for monitoring at least one patient characteristic during total intravenous anesthesia of the patient; and a storage cabinet associated with said housing for storing consumable materials for total intravenous anesthesia.

26. An apparatus for administering total intravenous anesthesia to a patient, the apparatus comprising:

a housing;

at least one supply of at least one intravenous anesthesia agent carried by the housing;

intravenous delivery means carried by the housing for controllably intravenously delivering said at least one intravenous anesthesia agent to the patient so that total intravenous anesthesia is achieved in the patient and without an inhaled anesthesia agent;

said at least one intravenous anesthesia agent comprising a first intravenous anesthesia agent having a relatively quick offset so that effects thereof wear off relatively quickly upon stopping intravenous infusion; and telecommunication means carried by said housing for providing at least one of a telemetry channel and a voice communications channel during total intravenous anesthesia of the patient, wherein said telecommunications means comprises a wireless transceiver.

27. An apparatus according to claim 27 wherein said wireless transceiver comprises a cellular telephone network transceiver.

28. An apparatus according to claim 26 wherein said at least one supply comprises at least one intravenous fluid bag; and wherein said intravenous infusion means comprises at least one intravenous infusion pump.

29. An apparatus according to claim 26 wherein said first intravenous anesthesia agent comprises an analgesic.

30. An apparatus according to claim 26 wherein the relatively quick offset of said first intravenous anesthesia agent is defined by a relatively short biological half-life not greater than about 10 minutes.

31. An apparatus according to claim 26 wherein said first intravenous anesthesia agent comprises an esterase metabolized opioid.

32. An apparatus according to claim 26 wherein said first intravenous anesthesia agent comprises remifentanil.

33. An apparatus according to claim 26 further comprising a battery carried by said housing for powering the apparatus.

34. An apparatus according to claim 26 wherein said housing has an upper surface defining a horizontal work surface.

35. An apparatus according to claim 26 further comprising castor means on a lower portion of said housing to permit relocation of said housing.

36. An apparatus according to claim 26 wherein said at least one supply comprises a second supply of a second intravenous anesthesia agent carried by said housing.

37. An apparatus for administering total intravenous anesthesia to a patient, the apparatus comprising:

a housing;

at least one supply of at least one intravenous anesthesia agent carried by the housing;

intravenous delivery means carried by the housing for controllably intravenously delivering said at least one, intravenous anesthesia agent to the patient so that total intravenous anesthesia is achieved in the patient and without an inhaled anesthesia agent;

said at least one intravenous anesthesia agent comprising a first intravenous anesthesia agent having a relatively quick offset so that effects thereof wear off relatively quickly upon stopping intravenous infusion; and telecommunication means carried by said housing for providing at least one of a telemetry channel and a voice communications channel during total intravenous anesthesia of the patient;

wherein said at least one supply comprises a second supply of a second intravenous anesthesia agent carried by said housing, and wherein said first intravenous anesthesia agent comprises an analgesic, and wherein said second intravenous anesthesia agent comprises a relatively quick offset amnestic.

38. An apparatus for administering total intravenous anesthesia to a patient, the apparatus comprising:

a housing;

at least one supply of at least one intravenous anesthesia agent carried by the housing;

intravenous delivery means carried by the housing for controllably intravenously delivering said at least one intravenous anesthesia agent to the patient so that total intravenous anesthesia is achieved in the patient and without an inhaled anesthesia agent;

said at least one intravenous anesthesia agent comprising a first intravenous anesthesia agent having a relatively quick offset so that effects thereof year off relatively quickly upon stepping intravenous infusion;

telecommunication means carried by said housing for providing at least one of a telemetry channel and a voice communications channel during total intravenous anesthesia of the patient; and a storage cabinet associated with said housing for storing consumable materials for total intravenous anesthesia.

39. A method for administering total intravenous anesthesia to a patient, the method comprising the steps of:

providing a housing carrying at least one supply of at least one intravenous anesthesia agent, at least one infusion pump for delivering said at least one intravenous anesthesia agent, and at least one patient characteristic monitor, the at least one monitor comprising at least an electrocardiogram;

controllably intravenously delivering said at least one intravenous anesthesia agent to the patient from the at least one respective supply carried by the housing and using the at least one infusion pump also carried by the housing so that total intravenous anesthesia is achieved in the patient, said at least one intravenous anesthesia agent comprising a first intravenous anesthesia agent having a relatively quick offset so that effects thereof wear off relatively quickly upon stopping intravenous infusion of said first intravenous anesthesia agent; and monitoring at least one patient characteristic using the at least one patient characteristic monitor carried by the housing during total intravenous anesthesia of the patient.

40. A method according to claim 39 wherein the step of monitoring comprises monitoring at least one of the patient's heart activity, blood oxygen level, carbon dioxide blood level, inspiration oxygen level, expiration oxygen level, inspiration carbon dioxide level, expiration carbon dioxide level, blood pressure, pulse rate, respiration rate and temperature.

41. A method for administering total intravenous anesthesia to a patient, the method comprising the steps of:

providing a housing carrying at least one supply of at least one intravenous anesthesia agent, at least one infusion pump for delivering said at least one intravenous anesthesia agent, and at least one patient characteristic monitor;

controllably intravenously delivering said at least one intravenous anesthesia agent to the patient from the at least one respective supply carried by the housing and using the at least one infusion pump also carried by the housing so that total intravenous anesthesia is achieved in the patient, said at least one intravenous anesthesia agent comprising a first intravenous anesthesia agent having a relatively quick offset so that effects thereof wear off relatively quickly upon stooping intravenous infusion of said first intravenous anesthesia agent; and monitoring at least one patient characteristic using the at least one patient characteristic monitor carried by the housing during total intravenous anesthesia of the patient;

wherein the step of providing further comprises the step of providing the housing having a wireless telecommunications transceiver carried by the housing; and further comprising the step of using the wireless telecommunications transceiver for providing at least one of a telemetry channel and a voice communications channel during total intravenous anesthesia of the patient.

42. A method according to claim 39 further comprising the step of recording at least one of the monitored patient characteristics.

43. A method according to claim 39 wherein the said first intravenous anesthesia agent comprises an analgesic.

44. A method according to claim 39 wherein the relatively quick offset of said first intravenous anesthesia agent is defined by a relatively short biological half-life not greater than about 10 minutes.

45. A method according to claim 39 wherein said first intravenous anesthesia agent comprises remifentanil.

* * * * *